US007250156B2

(12) United States Patent
Vernaire et al.

(10) Patent No.: US 7,250,156 B2
(45) Date of Patent: Jul. 31, 2007

(54) SOLID PHOTOPROTECTIVE COMPOSITIONS COMPRISING OCTENYLSUCCINIC ANHYDRIDE-ESTERIFIED STARCH SALTS

(75) Inventors: Sandrine Vernaire, Sevres (FR); Martin Josso, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 11/034,727

(22) Filed: Jan. 14, 2005

(65) Prior Publication Data

US 2005/0207999 A1     Sep. 22, 2005

Related U.S. Application Data

(62) Division of application No. 10/986,192, filed on Nov. 12, 2004, now abandoned.

(60) Provisional application No. 60/534,113, filed on Jan. 5, 2004.

(30) Foreign Application Priority Data

Nov. 17, 2003  (FR) .................................. 03 50843

(51) Int. Cl.
*A61Q 17/00* (2006.01)
*A61Q 17/04* (2006.01)
*A61Q 19/00* (2006.01)
*A61K 8/02* (2006.01)
*A61K 8/04* (2006.01)

(52) U.S. Cl. .................. 424/59; 424/60; 424/400; 424/40

(58) Field of Classification Search .................. 424/59, 424/60, 400, 401
See application file for complete search history.

(56) References Cited

U.S. PATENT DOCUMENTS

| 4,894,222 A | 1/1990 | Matravers |
| 5,256,404 A | 10/1993 | Martino et al. |
| 5,643,557 A | 7/1997 | Eteve et al. |
| 6,849,250 B2 * | 2/2005 | Candau ..................... 424/59 |
| 2003/0219391 A1 | 11/2003 | Liew et al. |

FOREIGN PATENT DOCUMENTS

| EP | 0 418 443 A1 | 3/1991 |
| EP | 0 518 772 A1 | 12/1992 |
| EP | 0 583 756 A2 | 2/1994 |

OTHER PUBLICATIONS

French Search Report corresponding to FR 03/50843 issued on Aug. 4, 2004.
Akira Akiu et al., Fragrance Journal, Jul. 1991, pp. 31-36.

* cited by examiner

*Primary Examiner*—Shelley A. Dodson
(74) *Attorney, Agent, or Firm*—Buchanan, Ingersoll & Rooney, PC

(57) ABSTRACT

Topically applicable, solid UV-photoprotecting compositions suited for the UV-photoprotection and/or makeup and/or care of the lips and/or the face, advantageously shaped as sticks, contain a) at least one fatty phase, a UV-photoprotecting amount of b) at least one organic UV-screening agent and c) a fraction of metal oxide mineral nanopigments, and d) an SPF-increasing amount of at least one octenylsuccinic anhydride-esterified starch salt, formulated into a physiologically acceptable medium therefor.

89 Claims, No Drawings

SOLID PHOTOPROTECTIVE COMPOSITIONS COMPRISING OCTENYLSUCCINIC ANHYDRIDE-ESTERIFIED STARCH SALTS

CROSS-REFERENCE TO PRIORITY/PROVISIONAL/PARENT APPLICATIONS

This application is a divisional of Ser. No. 10/986,192, filed Nov. 12, 2004 now abandoned, and claims priority under 35 U.S.C. § 119 of FR 03/50843, filed Nov. 17, 2003, and of provisional application Ser. No. 60/534,113, filed Jan. 5, 2004, each hereby expressly incorporated by reference and each assigned to the assignee hereof.

BACKGROUND OF THE INVENTION

1. Technical Field of the Invention

The present invention relates to solid photoprotective compositions comprising, formulated into a physiologically acceptable medium:
  a) at least one fatty phase,
  b) at least one organic UV-screening agent,
  c) at least a fraction of metal oxide-based mineral nanopigments, and
  d) at least one octenylsuccinic anhydride-esterified starch salt.

The present invention also relates to the use of at least one octenylsuccinic anhydride-esterified starch salt in a solid photoprotective composition comprising at least one fatty phase, at least one organic UV-screening agent and at least a fraction of metal oxide-based mineral nanopigments, with the aim of increasing the sun protection factor.

2. Description of Background and/or Related and/or Prior Art

It is well known that light radiation with wavelengths of between 280 nm and 400 nm permits tanning of the human epidermis and that light rays with wavelengths of between 280 and 320 nm, which are known as UV-B, cause skin burns and erythema that may be harmful to the development of a natural tan; this UV-B radiation should thus be screened out.

It is also known that UV-A rays with wavelengths of between 320 and 400 nm, which cause tanning of the skin, are liable to effect impairment therein, especially in the case of sensitive skin or of skin that is continually exposed to sunlight. UV-A rays in particular cause a loss of elasticity of the skin and the appearance of wrinkles, leading to premature aging. They promote triggering of the erythemal reaction or amplify this reaction in the case of certain individuals and may even be the cause of phototoxic or photoallergic reactions. It is thus desirable also to screen our UV-A radiation.

Many cosmetic compositions for photoprotecting the skin are known to this art.

They generally contain, in varying concentrations, one or more standard liposoluble organic screening agents and/or standard water-soluble organic screening agents capable of selectively absorbing the harmful UV rays, these screening agents (and the amounts thereof) being selected as a function of the desired sun protection factor, the sun protection factor (SPF) being expressed mathematically by the ratio of the dose of UV radiation required to reach the erythema-forming threshold with the UV-screening agent to the dose of UV radiation required to reach the erythema-forming threshold without UV-screening agent.

To provide antisun/sunscreen compositions with high sun protection factors in order to render same more effective and to reduce the contents of organic UV-screening agents for reasons of skin tolerance, it is common practice to include screening systems containing organic UV-screening agents combined with mineral agents for screening out UV radiation, such as nanopigments of metal oxide ($TiO_2$ or ZnO)

The formulation forms most commonly used for antisun products are emulsions. Mention may be made firstly of direct emulsions of oil-in-water type (i.e., a cosmetically and/or dermatologically acceptable support comprising an aqueous dispersing continuous phase and a fatty dispersed discontinuous phase) or inverse emulsions of the water-in-oil type (aqueous phase dispersed in a continuous fatty phase), which contains, in varying concentrations, one or more standard liposoluble organic screening agents and/or standard water-soluble organic screening agents. In such emulsions, the hydrophilic screening agents are present in the aqueous phase and the lipophilic screening agents are present in the fatty phase. In such emulsions, the metal oxide nanopigments, depending on their hydrophilic or hydrophobic nature, are dispersed in the aqueous or oily phase.

These emulsions are generally in the form of creams, lotions or milks. They are difficult to spread and to deposit on the lips or on certain sensitive areas of the face such as the contour of the eyes, the nose, the cheekbones or scars due to the fact that the product may run onto the area to be protected at the time of use.

To solve this problem, numerous products in solid form are known in the cosmetics industry in the field of care of the lips or of these sensitive areas of the face. Mention may especially be made, in the field of lipcare, of lip-repairing pencils, antisun sticks and moisturizing sticks. Specifically, it is particularly advantageous to have products in solid form, since such products are very practical to use and easy to transport. They allow good spreading and good deposition on the lips or other areas of the face.

The current sticks for photoprotecting the lips and the face contain as antisun/sunscreen emulsions screening systems containing both organic UV-screening agents and mineral screening agents.

There is an ever-increasing need to obtain in this type of support high sun protection factors without increasing the content of UV-screening agents present in the composition, for reasons of skin tolerance.

SUMMARY OF THE INVENTION

It has now surprisingly and unexpectedly been found that the addition of at least one octenylsuccinic anhydride-esterified starch salt into a solid photoprotective composition based on organic UV-screening agents and metal oxide nanopigments substantially increases the sun protection factor (SPF) without affecting the stability and disintegration properties of the stick. This substantial increase in the SPF of antisun/sunscreen sticks based on organic UV-screening agents and nanopigments is all the more surprising since said octenylsuccinic anhydride-esterified starch salt does not allow this effect to be obtained in a standard antisun emulsion based on the same screening system.

Thus, the present invention features solid photoprotective compositions comprising, formulated into a physiologically acceptable medium:
  a) at least one fatty phase,
  b) at least one organic UV-screening agent,
  c) at least a fraction of metal oxide-based mineral nanopigments, and d) at least one octenylsuccinic anhydride-esterified starch salt.

The present invention also features the use of at least one octenylsuccinic anhydride-esterified starch salt in a solid photoprotective composition comprising at least one fatty phase, at least one organic UV-screening agent and at least a fraction of metal oxide-based mineral nanopigments, for increasing the sun protection factor thereof.

DETAILED DESCRIPTION OF BEST MODE AND SPECIFIC/PREFERRED EMBODIMENTS OF THE INVENTION

Since the solid compositions according to the invention are intended for topical application, especially to the face and the lips, they comprise a physiologically acceptable medium. The term "physiologically acceptable medium" means herein a non-toxic medium that may be applied to the face, in particular the nose, the contour of the eyes, the cheeks or the lips. The composition of the invention may especially constitute a cosmetic or dermatological composition.

Moreover, for the purposes of the present invention, the term "solid composition" means any composition that does not run under its own weight and that has a hardness as defined below.

The hardness and thus the shear force of the composition according to the invention should preferably be such that the composition is self-supporting, i.e., it supports itself while remaining in its solid form (for example a wand) and does not collapse under its own weight as do creams or liquids, and same can be easily disintegrated to form a satisfactory deposit on the skin and the lips. The hardness of the sticks obtained is measured at 20° C. using a DFGHS 2 tensile testing machine from the company Indelco-Chatillon, traveling at a speed of 100 mm/minute. It is expressed as the sheer force (expressed in grams) required to cut a stick 12.7 mm in diameter under these conditions. In the present invention, the shear force of the composition preferably ranges from 100 to 300 g, better still from 120 to 250 g and even better still from 150 to 220 p.

In general, the compositions according to the invention are solid and may be in the form of a cast product or a product in a dish or in the form of a stick.

The metal oxide-based mineral nanopigments according to the present invention are powders of particles having a mean elementary size of less than 100 nm, generally between 5 nm and 100 nm and preferably between 10 and 50 nm. The metal oxides forming these nanopigments may be chosen especially from coated or uncoated titanium oxide, iron oxide, zinc oxide, zirconium oxide and cerium oxide. Titanium oxide, amorphous or in crystalline form (rutile and/or anatase form), is most particularly preferred among these oxides. These nanopigments may be coated with a hydrophobic coating. These nanopigments and the use thereof as photoprotective agents are known and described, for example, in EP-518,772 and EP-518,773.

The metal oxide nanopigments with hydrophobic coating according to the invention may have undergone, for example, one or more treatments with one or more compounds selected from among alumina, silica, aluminum derivatives (for example the stearate and laurate), silicon compounds (for example silicones, polydimethylsiloxanes, alkoxysilanes or siloxysilicates), sodium compounds, iron oxides, iron esters (for example the stearate), fatty acids, fatty alcohols and derivatives thereof (such as stearic acid, hydroxystearic acid, stearyl alcohol, hydroxystearyl alcohol and lauryl alcohol, and derivatives thereof), lecithin, waxes (for example carnauba wax), (meth)acrylic polymers (for example polymethylmethacrylates) and fluoro compounds (for example perfluoroalkyl compounds and perfluoroalkyl ethers). The oxides may also be treated with a mixture of these compounds or they may comprise several of these successive coatings.

More particularly, the metal oxides with a hydrophobic coating in the compositions of the invention may be selected from among nanotitanium oxides treated with:

alumina and stearic acid, for instance the product sold under the name UV-Titan M160 by Kemira, and the product sold under the name ST-430C by Inanata;

polydimethylsiloxanes (PDMS), for instance the products sold under the name Eusolex T-2000 by Merck, under the name UV Titan X170 by Eckart, or under the name Si-UFTR-Z by Myoshi;

alkoxysilanes, for instance the product sold under the name Covascreen T1 by Wackherr;

perfluoroalkyl compounds, for instance the product sold under the name PF-7 $TiO_2$ MT-600B by Daito;

perfluoroalkyl ethers, for instance the product sold under the name $TiO_2$ VF-25-3A by Toshiki;

siloxysilicates, for instance the product sold under the name TSS-1 by ISK;

polymethyl methacrylates, for instance the product sold under the name PW Covasil S by Wackherr;

lecithin, for instance the product sold under the name Duotarc CW 5-25 by Sachtleben;

carnauba wax, for instance the product sold under the name UVT-PT 951101 by Kemira;

silica and alumina, for instance the products sold under the names Microtitanium Dioxide MT 500 SA and Microtitanium Dioxide MT 100 SA by Tayca, and Tioveil FIN, Tioveil OP, Tioveil MOTG and Tioveil IPM by Uniqema;

alumina and aluminum stearate, for instance the product sold under the name Microtitanium Dioxide MT 100 T by Tayca;

alumina and aluminum laurate, for instance the product sold under the name Microtitanium Dioxide MT 100 S by Tayca;

iron oxides and iron stearate, for instance the product sold under the name Microtitanium Dioxide MT 100 F by Tayca;

silica, alumina and silicone, for instance the products sold under the names Microtitanium Dioxide MT 100 SAS, Microtitanium Dioxide MT 600 SAS and Microtitanium Dioxide MT 500 SAS by Tayca;

octyltrimethoxysilane, for instance the product sold under the name T-805 by Degussa or the product sold under the name Uvinul $TiO_2$ by BASF;

alumina and glycerol, for instance the product sold under the name UVT-M212 by Kemira; and alumina and silicone, for instance the product sold under the name UVT-M262 by Kemira.

These hydrophobic coated nanotitanium oxides may be in the form of a solid filler or in the form of a dispersion in an oily medium. Examples of dispersions of coated titanium oxide that may be mentioned include the products indicated above, sold by Uniqema under the names Tioveil FIN (nanotitanium oxide dispersed in $C_{12}$-$C_{15}$ alkyl benzoate, with a hydroxystearic acid polycondensate as dispersant) and Tioveil MOTG (nanotitanium oxide dispersed in mineral oil/triglycerides, with a hydroxystearic acid polycondensate as dispersant); the product sold under the name Covascreen TI by Wackherr (oily dispersion of $TiO_2$ coated with trimethoxyoctylsilane at 60%); the product sold under the name Daitopersion TI-30 by Daito (dispersion of nanotitanium oxide coated with polymethylhydrogenosiloxane in cyclomethicone and dimethicone copolyol); the product sold under the name Tiosphere Ultra by Collaborative Laboratories (nanotitanium oxide coated with stearic acid/alumina, dispersed in 2-ethylhexyl hydroxystearate benzoate); the product sold under the name Mibrid Dispersion SAS4 5050 by Myoshi (nanotitanium oxide coated with alumina/stearic acid and then with polydimethylsiloxane, dispersed in cyclopentasiloxane); the product sold under the name SPD-T1 by Shin-Etsu (nanotitanium oxide coated with a silicone-grafter acrylic polymer and dispersed in cyclopentedimethylsiloxane).

As examples of zinc oxides that may be included in the compositions of the invention, mention may be made of the nanozinc oxide dispersions sold under the names Daitopersion Zn-30 and Zn-50 by Daito, which are dispersions in cyclopolymethylsiloxane/oxyethylenated polydimethylsiloxane, containing 30% or 50% of nanozinc oxides coated with polymethylhydrogenosiloxane.

One or more kinds of coated metal oxides may be included in the compositions of the invention.

Octyltrimethoxysilane-treated $TiO_2$ nanopigments, for instance the commercial products T-805 and Uvinul $TiO_2$, will more particularly be incorporated.

The nanopigments in accordance with the invention are generally present in the subject compositions in proportions ranging from 0.01% to 20% by weight relative to the total weight of the composition, and preferably ranging from 0.1% to 10% by weight relative to the total weight of the composition.

Among the octenylsuccinic anhydride-esterified starch salts that may be formulated according to the invention, mention may be made of the calcium, sodium or aluminum salts obtained by reacting octenylsuccinic anhydride with a maize starch, and in particular the following esterified maize starch salts designated below under their INCI name:

aluminum starch octenylsuccinate sold especially under the trademark "Dry Flo Plus" or "Dry Flo Pure" by National Starch;

sodium starch octenylsuccinate sold especially under the trademark "Capsul" by National Starch;

calcium starch octenylsuccinate sold under the trademark "Skin Flow-C" by Midwest Grain Products Aluminum starch octenylsuccinate will more particularly be used.

The octenylsuccinic anhydride-esterified starch salts in accordance with the invention are preferably present in concentrations ranging from 0.1% to 10% by weight and more preferably from 1% to 5% by weight relative to the total weight of the composition.

The organic UV-screening agents in accordance with the invention are selected especially from among anthranilates; cinnamic derivatives; dibenzoylmethane derivatives; salicylic derivatives; camphor derivatives; triazine derivatives such as those described in U.S. Pat. No. 4,367,390, EP-863, 145, EP-517,104, EP-570,838, EP-796,851, EP-775,698, EP-878,469, EP-933,376, EP-507,691, EP-507,692, EP-790,243, EP-944,624; benzophenone derivatives; β,β-diphenylacrylate derivatives; benzotriazole derivatives; benzalmalonate derivatives; benzimidazole derivatives; imidazolines; bis-benzazolyl derivatives as described in EP-669, 323 and U.S. Pat. No. 2,463,264; p-aminobenzoic acid (PABA) derivatives; methylenebis(hydroxyphenylbenzotriazole) derivatives as described in U.S. Pat. Nos. 5,237,071, 5,166,355, GB-2,303,549, DE-197,26,184 and EP-893,119; benzoxazole derivatives as described in EP-0,832,642, EP-1,027,833, EP-1,300,137 and DE-101,62,844; screening polymers and screening silicones such as those described especially in WO 93/04665; α-alkylstyrene-based dimers, such as those described in DE-198,55,649; 4,4-diarylbutadienes such as those described in EP-0,967,200, DE-197, 46,654, DE-197,55,649, EP-A-1,008,586, EP-1,133,980 and EP-133,981 and mixtures thereof.

As examples of organic screening agents, mention may be made of those denoted hereinbelow under their INCI name:

Para-Aminobenzoic Acid Derivatives:
PABA,
Ethyl PABA,
Ethyl dihydroxypropyl PAPA,
Ethy dimethyl PABA sold in particular under the name "Escalol 507" by ISP,
Glyceryl PABA,
PEG-25 PABA sold under the name "Uvinul P25" by BASF.

Salicylic Derivatives:
Homosalate sold under the name "Eusolex HMS" by Rona/EM Industries,
Ethylhexyl salicylate sold under the name "Neo Heliopan OS" by Haarmann and Reimer,
Dipropylene glycol salicylate sold under the name "Dipsal" by Scher,
TEA salicylate sold under the name "Neo Heliopan TS" by Haarmann and Reimer.

Dibenzoylmethane Derivatives:
Butyl methoxydibenzoylmethane sold in particular under the trademark "Parsol 1789" by Roche Vitamins,
Isopropyldibenzoylmethane.

Cinnamic Derivatives:
Ethylhexyl methoxycinnamate sold in particular under the trademark "Parsol MCX" by Roche Vitamins,
Isopropyl methoxycinnamate,
Isoamyl methoxycinnamate sold under the trademark "Neo Heliopan E 1000" by Haarmann and Reimer,
Cinoxate, DEA methoxycinnamate, diisopropyl methylcinnamate,
Glyceryl ethylhexanoate dimethoxycinnamate.

β,β-Diphenylacrylate Derivatives:
Octocrylene sold in particular under the trademark "Uvinul N539" by BASF,
Etocrylene sold in particular under the trademark "Uvinul N35" by BASF.

Benzophenone Derivatives:
Benzophenone-1 sold under the trademark "Uvinul 400" by BASF,
Benzophenone 2 sold under the trademark "Uvinul D50" by BASF,
Benzophenone-3 or Oxybenzone sold under the trademark "Uvinul M40" by BASF,
Benzophenone4 sold under the trademark "Uvinul MS40" by BASF,
Benzophenone-5,
Benzophenone-6 sold under the trademark "Helisorb 11" by Norquay,
Benzophenone-8 sold under the trademark "Spectra-Sorb U-24" by American Cyanamid,
Benzophenone-9 sold under the trademark "Uvinul DS49" by BASF,
Benzophenone-12,
n-Hexyl 2-(4-diethylamino-2-hydroxybenzoyl)benzoate sold under the trademark "Uvinul A Plus" by BASF.

Benzylidenecamphor Derivatives:
3-Benzylidenecamphor manufactured under the name "Mexoryl SD" by Chimex, 4-Methylbenzylidenecamphor sold under the name "Eusolex 6300" by Merck, Benzylidenecamphorsulfonic acid manufactured under the name "Mexoryl SL" by Chimex, Camphor benzalkonium methosulfate manufactured under the name "Mexoryl SO" by Chimex, Terephthalylidenedicaphorsulfonic acid manufactured under the name "Mexoryl SX" by Chimex, Polyacrylamidomethybenzylidenecamphor manufactured under the name "Mexoryl SW" by Chimex.

Phenylbenzimidazole Derivatives:

Phenylbenzimidazolesulfonic acid sold in particular under the trademark "Eusolex 232" by Merck, Disodium phenyl dibenzimidazole tetrasulfonate sold under the trademark "Neo Heliopan AP" by Haarmann and Reimer.

Triazine Derivatives:

Anisotriazine sold under the trademark "Tinosorb S" by Ciba Geigy,

Ethylhexyltriazone sold in particular under the trademark "Uvinul T150" by BASF, Diethylhexylbutamidotriazone sold under the trademark "Uvasorb HEB" by Sigma 3V.

Phenylbenzotriazole Derivatives:

Drometrizole trisiloxane sold under the name "Silatrizole" by Rhodia Chimie,

Methylenebis (benzotriazolyl) tetramethylbutylphenol sold in solid form under the trademark "Mixxim BB/100" by Fairmount Chemical, or in micronized form as an aqueous dispersion under the trademark "Tinosorb M" by Ciba Specialty Chemicals.

Anthranilic Derivatives:

Menthyl anthranilate sold under the trademark "Neo Heliopan MA" by Haarmann and Reimer.

Imidazoline Derivatives:

Ethylhexyldimethoxybenzylidenedioxoimidazoline propionate.

Benzalmalonate Derivatives:

Polyorganosiloxanes containing benzalmalonate functions, such as Polysilicone-15 sold under the trademark "Parsol SLX" by Roche Vitamins.

4,4-Diarylbutadiene Derivatives:

1,1-Dicarboxy(2,2'-dimethylpropyl)-4,4-diphenylbutadiene.

Benzoxazole Derivatives:

2,4-Bis[5-1 (dimethylpropyl)benzoxazol-2-yl(4-phenyl) amino]-6-(2-ethylhexyl)imino-1,3,-triazine sold under the name Uvasorb K2A by Sigma 3V, and mixtures thereof.

The organic UV-screening agents that are preferred are selected from among:

Ethylhexyl salicylate,
Ethylhexyl methoxycinnamate,
Butyl methoxydibenzoylmethane,
Octocrylene,
Phenylbenzimidazolesulfonic acid,
Benzophenone-3,
Benzophenone-4,
Benzophenone-5,
n-Hexyl 2-(4-diethylamino-2-hydroxybenzoyl)benzoate,
4-Methylbenzylidenecamphor,
Terephthalylidenedicamphorsulfonic acid,
Disodium phenyldibenzimidazoletetrasulfonate,
Anisotriazine,
Ethylhexyltriazone,
Diethylhexylbutamidotriazone,
Methylenebis(benzotriazolyl)tetramethylbutylphenol,
Drometrizole trisiloxane,
Polysilicone-15,
1,1-Dicarboxy(2,2'-dimethylpropyl)-4,4-diphenylbutane,
2,4-Bis[5-1(dimethylpropy)benzoxazol-2-yl(4-pheny) imino]-6-(2-ethylhexyl)imino-1,3,5-triazine and mixtures thereof.

The organic UV-screening agents in accordance with the invention are generally present in the subject compositions in proportions ranging from 0.01% to 20% by weight relative to the total weight of the composition, and preferably ranging from 0.1% to 10% by weight relative to the total weight of the composition.

According to one particular embodiment of the invention, the composition comprises a screening system containing at least butylmethoxydibenzoylmethane, octocrylene and titanium oxide nanopigments.

According to another particular embodiment of the invention, the composition comprises a screening system containing at least butylmethoxydibenzoylmethane, octocrylene, drometrizole trisiloxane and titanium oxide nanopigments.

The compositions of the invention preferably comprise only one fatty phase, and this fatty phase is preferably a continuous phase.

The compositions of the invention may be anhydrous compositions, i.e., compositions free of water or of hydrophilic compounds, but it is also possible for them not to be anhydrous and in this case to comprise up to 10% by weight of hydrophilic phase relative to the total weight of the composition, and preferably 1% to 5% by weight of hydrophilic phase relative to the total weight of the composition, the hydrophilic phase comprising water alone, or of water and of hydrophilic and water-soluble additives such as polyols, gelling agents and/or active agents. If this hydrophilic phase is present, it is preferably dispersed in the fatty phase that forms a continuous phase.

According to one particular embodiment of the invention, the composition comprises a hydrophilic phase comprising at least one water-soluble UV-screening agent.

Among the water-soluble UV-screening agents that may be used, mention may be made of phenylbenzimidazolesulfonic acid, terephthalylidenedicamphorsulfonic acid, disodium phenyldibenzimidazoletetrasulfonate, Benzophenone-4.

The terephthalylidenedicamphorsulfonic acid sold under the name "Mexoryl SX" by Chimex will more particularly be used as water-soluble UV-screening agent.

According to one particular embodiment of the invention, the composition is anhydrous, i.e., it comprises only the fatty phase, or virtually anhydrous, i.e., it comprises less than 5% by weight of hydrophilic phase (water and/or hydrophilic or water-soluble additives).

The fatty phase of the compositions according to the invention generally comprises at least one oil and at least one wax.

For the purposes of the present invention, the term "oil" means any physiologically acceptable non-aqueous medium that is liquid at room temperature (25° C.) and atmospheric pressure (760 mm Hg).

For the purposes of the present invention, the term "wax" means any lipophilic fatty compound that is solid at room temperature (25° C.), with a reversible solid/liquid change of state, having a melting point of greater than 40° C., which may be up to 200° C., and having in the solid state an anisotropic crystal organization.

The oils in accordance with the invention may be hydrocarbon-based oils and/or silicone oils and/or fluoro oils. They may be of animal, plant, mineral or synthetic origin.

The term "hydrocarbon-based oil" means any oil predominantly comprising carbon and hydrogen atoms, and possibly ester, ether, fluoro, carboxylic acid and/or alcohol groups. In addition, the oils used may be volatile and/or non-volatile.

The term "volatile oil" means an oil capable of evaporating at room temperature from a support onto which it has been applied, in other words an oil having a measurable vapor pressure at 25° C. and 1 atmosphere, for example greater than 0 Pa, in particular ranging from $10^{-3}$ to 300 mm Hg (0.13 Pa to 40,000 Pa).

Volatile oils that may especially be mentioned include volatile silicone oils, such as linear or cyclic volatile silicones. Mention may also be made of volatile hydrocarbon-based oils such as isoparaffins, and volatile fluoro oils.

Among the oils that may be used in the compositions of the invention, some are polar and others are apolar (i.e., non-polar).

The polar oils comprise in their chemical structure at least one nonionic polar group and preferably at least two nonionic or ionic polar groups such as the following groups:

COOH;

monosubstituted or disubstituted OH (primary or secondary);

$PO_4$;

NHR; $NR_1R_2$, $R_1$ and $R_2$ optionally forming a ring and representing a linear or branched $C_1$ to $C_{20}$ alkyl or alkoxy radical, or

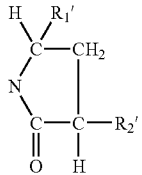

in which $R_1'$ and $R_2'$ may represent hydrogen or a linear or branched $C_1$ to $C_{20}$ alkyl or alkoxy chain.

The polarity may be described by the Hansen solubility parameter δa. Specifically, this parameter characterizes, for a given constituent, the energy corresponding to the polar interactions (δp) and the interactions of hydrogen bonding type (δh) existing between the molecules of this constituent.

$$\delta_a = \sqrt{\delta_p^2 + \delta_h^2}$$

The apolar oils have a δa value equal to 0. In particular, the apolar oils according to the invention may be selected in particular from among:

silicone oils, such as volatile or non-volatile, linear or cyclic polydimethylsiloxanes (PDMS) that are liquid at room temperature; phenylsilicones, for instance phenyl trimethicones, phenyl dimethicones, phenyltrimethylsiloxydiphenylsiloxanes, diphenyl dimethicones, diphenylmethyidiphenyltrisiloxanes and 2-phenylethyl trimethylsiloxysilicates;

linear or branched hydrocarbons of synthetic or mineral origin, for instance volatile or non-volatile liquid paraffins, and derivatives thereof; liquid petroleum jelly; liquid lanolin; polydecenes; hydrogenated polyisobutene such as Parleam® oil; squalane; hydrogenated isoparaffin; isohexadecane; isododecane;

and mixtures thereof.

The polar oils have a δa value other than 0, i.e., greater than 0. In particular, the polar oils used in the compositions of the invention may be selected from among:

oils of plant origin, hydrocarbon-based oils with a high content of triglycerides consisting of fatty acid esters of glycerol in which the fatty acids may have varied chain lengths from $C_4$ to $C_{24}$, these chains possibly being linear or branched, and saturated or unsaturated. As oils of plant origin, mention may be made, in particular, of jojoba oil, wheat germ oil, maize oil, sunflower oil, shea butter oil, castor oil, sweet almond oil, macadamia oil, apricot oil, soybean oil, cotton oil, alfalfa oil, poppy oil, pumpkin oil, sesame oil, marrow oil, rapeseed oil, avocado oil, hazelnut oil, grapeseed oil, blackcurrant seed oil, evening primrose oil, millet oil, barley oil, quinoa oil, olive oil, rye oil, safflower oil, candlenut oil, passionflower oil, musk rose oil and coriander oil; or alternatively caprylic/capric acid triglycerides such as those sold by Stearineries Dubois or those sold under the names Miglyol 810, 812 and 818 by Dynamit Nobel;

synthetic oils or synthetic esters of formula $R_5COOR_6$ in which $R_5$ represents a linear or branched fatty acid residue containing from 1 to 40 carbon atoms and $R_6$ represents an in particular branched hydrocarbon-based chain containing from 1 to 40 carbon atoms, on condition that $R_5+R_6 \geq 10$, such as, for example, purcellin oil (cetostearyl octanoate), isononyl isononanoate, $C_{12}$-$C_{15}$ alkyl benzoate, isopropyl myristate, 2-ethylhexyl palmitate, isostearyl isostearate, isopropyl isostearate, and alkyl or polyalkyl octanoates, decanoates or ricinoleates; hydroxylated esters such as isostearyl lactate and diisostearyl malate; $C_{12}$-$C_{15}$ alkyl benzoate; and pentaerythritol esters;

synthetic ethers containing from 10 to 40 carbon atoms;

$C_8$ to $C_{26}$ fatty alcohols such as oleyl alcohol, isostearyl alcohol and octyldodecanol;

mixtures thereof.

The amount of oil(s) may range, for example, from 20% to 80% by weight and preferably from 30% to 70% by weight relative to the total weight of the composition.

The waxes in accordance with the invention may be selected from among waxes of natural origin, especially of plant or animal origin, from waxes of mineral origin and from waxes of synthetic origin, and mixtures thereof. As waxes that may be used in the compositions of the invention, examples that may be mentioned include beeswax, montan wax, carnauba wax, candelilla wax, China wax, flax wax, pine wax, cotton wax, ouricury wax, lignite wax, rice bran wax, sugar cane wax, Japan wax, cork fiber wax, paraffin waxes, microcrystalline waxes, lanolin wax, ozokerites, hydrogenated oils with a melting point of greater than about 40° C. (approximately), for instance hydrogenated jojoba oil, polyethylene waxes derived from the polymerization of ethylene, waxes obtained by Fischer-Tropsch synthesis, fatty acid esters and glycerides that are concrete (i.e., solid) at 40° C., and silicone waxes, for instance alkyl, alkoxy- and/or esters of poly(di)methylsiloxane that are solid at 40° C.; and mixtures thereof.

The total amount of wax(es) may range, for example, from 5% to 40% by weight and preferably from 10% to 30% by weight relative to the total weight of the composition.

The fatty phase may also comprise at least one fatty substance of pasty consistency of butter type, such as shea butter and cocoa butter.

As indicated above, the compositions of the invention may comprise from 0% to 10% by weight and better still from 1% to 5% by weight, relative to the total weight of the composition, of a hydrophilic phase, which may comprise water and/or hydrophilic or water-soluble additives (for example water-soluble screening agents, vitamins and/or gelling agents). Same may especially comprise moisturizers such as glycerol. The hydrophilic constituents optionally present are preferably dispersed in the fatty phase comprising the oils and waxes.

The compositions according to the invention may comprise, in addition to the metal oxide nanopigments, particles chosen from pigments, nacres and fillers, and mixtures thereof.

These additional pigments, nacres and fillers are chosen from those usually used in cosmetic compositions.

The term "pigments" should be understood as meaning white or colored, mineral or organic particles for coloring and/or opacifying the composition.

The term "fillers" should be understood as meaning colorless or white, mineral or synthetic, lamellar or non-particles for giving the composition body or rigidity, and/or for giving the makeup softness, a matt effect and uniformity.

The term "nacres" should be understood as meaning iridescent particles that reflect light.

The additional pigments may be white or colored, mineral and/or organic, and of micrometric or nanometric size. Examples that may be mentioned include titanium dioxide, zirconium dioxide and cerium dioxide, and also zinc oxide, iron oxide, chromium oxide and ferric blue. Among the organic pigments that may be mentioned are carbon black and barium, strontium, calcium or aluminum lakes.

Among the nacres that may be included in the compositions of the invention, examples that may be mentioned include mica coated with titanium oxide, with iron oxide, with natural pigments or with bismuth oxychloride, and also colored titanium mica.

Fillers may be mineral or synthetic, and lamellar or non-lamellar. As fillers that may be used in the composition of the invention, examples that may be mentioned include talc, mica, silica, kaolin, nylon powders, polyethylene powders, Teflon, modified or unmodified starch, titanium mica, natural mother-of-pearl, boron nitride, microspheres such as Expancel (Nobel Industrie), Polytrap (Dow Corning) and silicone resin microbeads (for example Tospeals from Toshiba).

The compositions according to the invention may also comprise a dyestuff, which may be selected from among the lipophilic dyes and hydrophilic dyes usually used in cosmetic or dermatological compositions, and also from the pigments and nacres described above; and mixtures thereof. This dyestuff is generally present in a proportion of from 0.01% to 40% by weight and preferably from 5% to 25% by weight relative to the total weight of the composition.

The compositions according to the invention may also comprise any additive usually used in the field under consideration, especially in the cosmetics field, such as antioxidants; fragrances; essential oils; preservatives; cosmetic active agents; vitamins, for instance vitamin E (tocopherol) and derivatives thereof (for example the acetate), vitamin A (retinol) and derivatives thereof (for example retinyl palmitate), vitamin C (ascorbic acid) and derivatives thereof (for example ascorbyl palmitate), the derivatives of these vitamins especially being esters, including the palmitate and the acetate; essential fatty acids; sphingolipids and ceramides; surfactants; polymers; and mixtures thereof. These additives may be present in the composition in a proportion of from 0% to 20% by weight relative to the total weight of the composition.

Needless to say, one skilled in this art will take care to select this or these optional additional, compound(s) and/or the amount thereof, such that the advantageous properties of the composition according to the invention are not, or are not substantially, adversely affected by the envisaged addition.

As indicated above, the compositions according to the invention are in solid form. This means that no collapse of the composition is observed, in the absence of mechanical or thermal stimulation (especially heating), when it is outside the container comprising it.

The processes for manufacturing the compositions according to the invention do not differ in any way from the processes conventionally used in cosmetics, which are entirely familiar to those skilled in the art.

The compositions according to the invention may especially constitute a care product and/or a makeup product for the lips and/or the face, especially the nose, the contour of the eyes and the cheeks.

The makeup products are usually colored and generally contain pigments in the form of makeup products, the compositions of the invention may advantageously constitute a foundation, a lipstick, a makeup rouge or an eyeshadow.

This product may be in the form of a cast product, a product in a dish (foundation, makeup rouge or eyeshadow) or a product in the form of a wand (lips lipstick or lipcare stick). According to one preferred embodiment of the invention, it is in the form of a wand (stick), more particularly for photoprotecting the lips and/or the face.

In order to further illustrate the present invention and the advantages thereof, the following specific examples are given, it being understood that same are intended only as illustrative and in nowise limitative. In said examples to follow, all parts and percentages are given by weight, unless otherwise indicated.

Examples of Antisun Sticks:

| Ingredients | Stick 1 | Stick 2 |
|---|---|---|
| Octenylsuccinic anhydride-esterified maize starch, aluminum salt (Dry Flo Plus - National Starch) | 0 | 5 g |
| Carnauba wax | 5 g | 5 g |
| Candelilla wax | 8 g | 8 g |
| Polyethylene wax | 7 g | 7 g |
| Hydrophobic fumed silica (Aerosil R 972 - Degussa) | 0.23 g | 0.23 g |
| Castor oil | 12 g | 12 g |
| Hydrogenated isoparaffin (6–8 mol of isobutylene) | 15 g | 15 g |
| Shea butter | 3.5 g | 3.5 g |
| Cocoa butter | 3.5 g | 3.5 g |
| 4-tert-Butyl-4'-methoxydibenzoylmethane (Parsol 1789 - Roche Vitamins) | 3 g | 3 g |
| Octocrylene (Uvinul N539 - BASF) | 10 g | 10 g |
| Drometrizole trisiloxane (Silatrizole - Rhodia Chimie) | 1 g | 1 g |
| Octyltrimethoxysilane-treated rutile titanium oxide (25–40 nm) (Uvinul $TiO_2$ - BASF) | 1 g | 1 g |
| Terephthalylidenedicamphorsulfonic acid (Mexoryl SX - Chimex) | 1.5 g | 1.5 g |
| Talc | 3 g | 3 g |
| Mixture of natural tocopherols in soybean oil (50/50) | 0.2 g | 0.2 g |
| Crystalline sorbitol | 0.5 g | 0.5 g |
| Pentasodium salt of ethylenediamine-tetramethylenephosphonic acid (Dequest 2046 - Solutia) | 0.15 g | 0.15 g |
| Ascorbyl glucoside (Hayashibara) | 0.27 g | 0.27 g |
| Deionized water | 0.9 g | 0.9 g |
| Triethanolamine | qs | qs |
| Fragrance | qs | qs |
| Caprylic/capric acid triglycerides (60/40) (Miglyol 812 - Dynamit Nobel) | qs 100 g | qs 100 g |

Procedure:

The water, the terephthalylidenedicamphorsulfonic acid, the ascorbyl glucoside, the sorbitol, the D-panthenol and the pentasodium salt of ethylenediaminetetramethylenephosphonic acid are mixed together (aqueous phase).

The waxes, the oils and butters, the tocopherols and the fragrance are melted at 85° C. The liposoluble sunscreens, the talc, the modified starch and the titanium dioxide are then added. The silica dispersed in the castor oil is added. The aqueous phase is added. The mixture is homogenized for 10 minutes and cast into stick moulds.

Mixture of the In Vivo SPF:

For each of the antisun sticks 1 and 2 thus prepared, the sun protection factor (SPF) associated therewith was then determined. The measurement of the sun protection factor was performed on five volunteers according to the Colipa method reference 94/289 October 1984.

The sun protection factor (SPF) was then calculated mathematically by means of the ratio of the irradiation time required to reach the erythema-forming threshold with the UV-screening agent (protected area) to the time required to reach the erythema-forming threshold without UV-screening agent (unprotected area). The results in terms of mean sun protection factor (average for the five volunteers) obtained are reported in the table given below.

| Compositions | Mean in vivo SPF |
| --- | --- |
| Stick No. 1 (prior art) | 22 ± 3.1 |
| Stick No. 2 (invention) | 40 ± 12.2 |

The addition of aluminum starch octenylsuccinate to the antisun stick 2 makes it possible to substantially increase (i.e.: about twofold) the SPF relative to the antisun stick 1.

Test of the Influence of Aluminum Starch Octenylsuccinate on the SPF of a Formulation in the Form of a Liquid Water/Oil Emulsion:

The following W/O emulsions were prepared:

| Ingredients | Ex A | Ex B |
| --- | --- | --- |
| Octenylsuccinic anhydride-esterified maize starch, aluminum salt (Dry Flo Plus - National Starch) | 0 | 5 g |
| $C_{12}$–$C_{15}$ alkyl benzoate | 6 g | 6 g |
| Cyclohexasiloxane | 8 g | 8 g |
| Cyclopentasiloxane | 8 g | 8 g |
| Mixture of natural tocopherols in soybean oil (50/50) | 0.2 g | 0.2 g |
| Lauryl PEG/PPG-18/18 methicone (DC 5200 - Dow Corning) | 2 g | 2 g |
| PEG-30 dipolyhydroxystearate (Arlacel P135 - Uniqema) | 2 | 2 g |
| 4-tert-Butyl-4'-methoxydibenzoylmethane (Parsol 1789 - Roche Vitamins) | 3 g | 3 g |
| Octocrylene (Uvinul N539 - BASF) | 10 g | 10 g |
| Drometrizole trisiloxane (Silatrizole - Rhodia Chimie) | 1 g | 1 g |
| Octyltrimethoxysilane-treated rutile titanium oxide (25–40 nm) (Uvinul $TiO_2$ - BASF) | 1 g | 1 g |
| Terephthalylidenecamphorsulfonic acid (Mexoryl SX - Chimex) | 1.5 g | 1.5 g |
| Propylene glycol | 4 g | 4 g |
| Glycerol | 4 g | 4 g |
| Ethylhexyl glycerol (Sensiva SC50 - Schulke & Mayr) | 0.75 g | 0.75 g |
| Denatured alcohol | 4.20 g | 4.20 g |
| Pentasodium salt of ethylenediamine-tetramethylenephosphonic acid (Dequest 2046 - Solutia) | 0.1 g | 0.1 g |
| NaCl | 1 g | 1 g |
| Triethanolamine | 1 g | 1 g |
| Deionized water | qs 100 g | qs 100 g |

Each emulsion A and B is applied to plates of quartz+Transpore at a rate of 1.4 mg/$cm^2$.

For each formulation A and B, the sun protection factor (SPF) was measured according to the in vitro method as described in the article by Diffey et al., in *J. Soc. Cosmet. Chem.*, 40-127-133 (1989); this method consists in determining the monochromatic SPF every 5 nm in the wavelength range 290-400 nm and in calculating the SPF according to a mathematical equation The measurements are taken on four areas of the plate and each formulation is tested five times (five plates). The mean SPF values are indicated in the following table:

| Compositions | Mean in vitro SPF |
| --- | --- |
| Emulsion A | 33.0 ± 4.2 |
| Emulsion B | 26.9 ± 2.4 |

The addition of aluminum starch octenylsuccinate to emulsion B does not increase the SPF relative to emulsion A.

It therefore has no effect on the SPF of an antisun composition of the W/O emulsion type containing a screening system consisting of 1% of $TiO_2$ nanopigments and organic UV-screening agents: 3% of 4-tert-butyl-4'-methodydibenzoylmethane, 10% of Octocrylene, 1% of Drometrizole Trisiloxane and 1.5% of terephthalylidenedicamphorsulfonic acid, in contrast with an antisun stick according to the invention containing the same screening system.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable, solid UV-photoprotecting composition, comprising a) at least one fatty phase containing at least one oil and at least one wax, a UV-photoprotecting amount of b) at least one organic UV-screening agent and c) a fraction of metal oxide mineral nanopigments consisting of particles with a mean elementary size of less than 100 nm, and d) at least one octenylsuccinic anhydride-esterified starch salt, formulated into a physiologically acceptable medium therefor, said composition being a solid having a shear force ranging from 100 to 300 g.

2. The solid UV-photoprotective composition as defined by claim 1, said metal oxide mineral nanopigments having a mean elementary size ranging from 5 nm to 100 nm.

3. The solid UV-photoprotective composition as defined by claim 2, said nanopigments comprising coated or uncoated titanium oxide, iron oxide, zinc oxide, zirconium oxide and/or cerium oxide.

4. The solid UV-photoprotective composition as defined by claim 3, said nanopigments comprising coated or uncoated titanium oxide in amorphous form or in rutile and/or anatase crystalline form.

5. The solid UV-photoprotective composition as defined by claim 1, said metal oxide nanopigments having a hydrophobic coating.

6. The solid UV-photoprotective composition as defined by claim 5, said nanopigments having a hydrophobic coating having been treated with one or more compounds selected from the group consisting of alumina, silica, aluminum compounds, silicon compounds, sodium compounds, iron oxides, iron esters, fatty acids, fatty alcohols and derivatives thereof, lecithin, waxes, (meth)acrylic polymers and fluoro compounds, and mixtures thereof.

7. A topically-applicable, solid UV-photoprotective composition, comprising a) at least one fatty phase containing at least one oil and at least one wax, a UV-photoprotecting amount of b) at least one organic screening agent and c) a fraction of metal oxide mineral nanopigments, said metal oxide nanopigments comprising octyltrimethoxysilane-coated titanium oxide nanopigments, and d) at least one octenylsuccinic anhydride-esterified starch salt, formulated into a physiologically acceptable medium therefor, said composition being a solid having a shear force ranging from 100 to 300 g.

8. The solid UV-photoprotective composition as defined by claim 1, said metal oxide nanopigments comprising from 0.01% to 20% by weight thereof.

9. The solid UV-photoprotective composition as defined by claim 1, said at least one esterified starch being selected from the group consisting of calcium, sodium and aluminum salts obtained by reacting octenylsuccinic anhydride with a maize starch.

10. The solid UV-photoprotective composition as defined by claim 9, said at least one esterified starch salt being selected from the group consisting of:
    aluminum starch octenylsuccinate,
    sodium starch octenylsuccinate, and
    calcium starch octenylsuccinate.

11. The solid UV-photoprotective composition as defined by claim 10, said at least one esterified starch salt comprising aluminum starch octenylsuccinate.

12. The solid UV-photoprotective composition as defined by claim 1, said at least one octenylsuccinic anhydride-esterified starch salt comprising from 0.1% to 10% by weight thereof.

13. The solid UV-photoprotective composition as defined by claim 1, said at least one organic UV-screening agent being selected from the group consisting of anthranilates; cinnamic derivatives; dibenzoylmethane derivatives; salicylic derivatives; camphor derivatives; triazine derivatives; benzophenone derivatives; β,β-diphenylacrylate derivatives; benzotriazole derivatives; benzalmalonate derivatives; benzimidazole derivatives; imidazolines; bis-benzoazolyl derivatives; p-aminobenzoic acid (PABA) derivatives; methylenebis (hydroxyphenylbenzotriazole) derivatives; screening polymers and screening silicones; a-alkyl-styrene-based dimers; 4,4-diarylbutadienes, and mixtures thereof.

14. The solid UV-photoprotective composition as defined by claim 13, said at least one organic UV-screening agent being selected from the group consisting of:

Ethyihexyl salicylate,
Ethylhexyl methoxycinnamate,
Butylmethoxydibenzoylmethane,
Octocrylene,
Phenylbenzimidazolesulfonic acid,
Benzophenone-3,
Benzophenone-4,
Benzophenone-5,
n-Hexyl 2-(4-diethylamino-2-hydroxybenzoyl) benzoate,
4-Methylbenzylidenecamphor,
Terephthalylidenedicamphorsulfonic acid,
Disodium phenyldibenzimidazoletetrasulfonate,
Anisotriazine,
Ethylhexyltriazone,
Diethylhexylbutamidotriazone,
Methylenebis (benzotriazolyl) tetramethylbutylphenol,
Drometrizole trisiloxane,
Polysilicone-15,
1,1-Dicarboxy (2-2'-dimethylpropyl)-4,4-diphenyl-butadiene,
2,4-Bis [5-1(dimethylpropyl)benzoxazol-2-yl(4-phenyl) imino]-6-(2-ethylhexyl)imino-1,3,5-triazine and mixtures thereof.

15. The solid UV-photoprotective composition as defined by claim 1, said at least one organic UV-screening agent comprising from 0.01% to 20% by weight thereof.

16. A topically applicable, solid UV-photoprotective composition comprising a) at least one fatty phase containing at least one oil and at least one wax, a UV-photoprotecting amount of b) butylmethoxydibenzoylmethane and octocrylene and c) a fraction of titanium oxide nanopigments, and d) at least one octenylsuccinic anhydride-esterified starch salt, formulated into a physiologically acceptable medium therefor, said composition being a solid having a shear force ranging from 100 to 300 g.

17. A topically applicable, solid UV-photoprotective composition comprising a) at least one fatty phase containing at least one oil and at least one wax, a UV-photoprotecting amount of b) butylmethoxydibenzoylmethane, octocrylene and drometrizole trisiloxane and c) a fraction of titanium oxide nanopigments, and d) at least one octenylsuccinic anhydride-esterified starch salt, formulated into a physiologically acceptable medium therefor, said composition being a solid having a shear force ranging from 100 to 300 g.

18. The solid UV-photoprotective composition as defined by claim 1, comprising one continuous fatty phase.

19. The solid UV-photoprotective composition as defined by claim 1, the same being anhydrous.

20. The solid UV-photoprotective composition as defined by claim 1, comprising up to 10% by weight of a hydrophilic phase.

21. The solid UV-photoprotective composition as defined by claim 20, comprising a hydrophilic phase containing at least one water-soluble UV-screening agent.

22. The solid UV-photoprotective composition as defined by claim 20, said at least one water-soluble UV-screening agent comprising terephthalylidenedicamphorsulfonic acid.

23. The solid UV-photoprotective composition as defined by claim 1, said at least one oil being selected from the group consisting of volatile or non-volatile, polar or apolar hydrocarbon-based oils and/or silicone oils and/or fluoro oils, of animal, plant, mineral or synthetic origin.

24. The solid UV-photoprotective composition as defined by claim 23, said at least one oil comprising from 20% to 80% by weight thereof.

25. The solid UV-photoprotective composition as defined by claim 1 said at least one wax being selected from the group consisting of waxes of natural origin, waxes of mineral origin and waxes of synthetic origin, and mixtures thereof.

26. The solid UV-photoprotective composition as defined by claim 25, said at least one wax comprising from 5% to 40% by weight thereof.

27. The solid UV-photoprotective composition as defined by claim 1, said at least one fatty phase also comprising at least one fatty substance of pasty consistency of butter type.

28. The solid UV-photoprotective composition as defined by claim 1, further comprising particles selected from the group consisting of pigments, nacres and fillers, and mixtures thereof.

29. The solid UV-photoprotective composition as defined by claim 1, comprising at least one dyestuff.

30. The solid UV-photoprotective composition as defined by claim 1, shaped as a stick.

31. The solid UV-photoprotective composition as defined by claim 1, shaped as a dish.

32. The solid UV-photoprotective composition as defined by claim 1, shaped as a cast product.

33. A regime or regimen for the makeup and/or care of the lips and/or the face, comprising topically applying thereon a thus effective amount of the solid UV-photoprotecting composition as defined by claim 1.

34. A regime or regimen for the UV-photoprotection of the lips and/or the face, comprising topically applying thereon a thus effective amount of a solid UV-photoprotecting composition which comprises a) at least one fatty phase containing at least one oil and at least one wax, a UV-photoprotecting amount of b) at least one organic UV-screening agent and c) a fraction of metal oxide mineral nanopigments consisting of particles with a mean elementary size of less than 100 nm, and d) at least one octenylsuccinic anhydride-esterified starch salt, formulated into a physiologically acceptable medium therefor, said composition being a solid having a shear force ranging from 100 to 300 g.

35. A method for increasing the sun protection factor of a solid UV-photoprotecting composition comprising a) at least one fatty phase containing at least one oil and at least one wax, a UV-photoprotecting amount of b) at least one organic UV-screening agent and c) a fraction of metal oxide mineral nanopigments consisting of particles with a mean elementary size of less than 100 nm, which comprises formulating therewith a thus effective amount of d) at least one octenylsuccinic anhydride-esterified starch salt, said composition being a solid having a shear force ranging from 100 to 300 g.

36. The solid UV-photoprotective composition as defined by claim 7, said metal oxide mineral nanopigments having a mean elementary size ranging from 5 nm to 100 nm, said nanopigments comprising coated titanium oxide in amorphous form or in rutile and/or anatase crystalline form.

37. The solid UV-photoprotective composition as defined by claim 7, said metal oxide nanopigments comprising from 0.01% to 20% by weight thereof, said at least one octenylsuccinic anhydride-esterified starch salt comprising from 0.1% to 10% by weight thereof, and said at least one organic UV-screening agent comprising from 0.01% to 20% by weight thereof.

38. The solid UV-photoprotective composition as defined by claim 7, said at least one esterified starch salt being selected from the group consisting of:
aluminum starch octenylsuccinate,
sodium starch octenylsuccinate, and
calcium starch octenylsuccinate.

39. The solid UV-photoprotective composition as defined by claim 38, said at least one esterified starch salt comprising aluminum starch octenylsuccinate.

40. The solid UV-photoprotective composition as defined by claim 7, said at least one organic UV-screening agent being selected from the group consisting of:
Ethylhexyl salicylate,
Ethylhexyl methoxycinnamate,
Octocrylene,
Phenylbenzimidazolesulfonic acid,
Benzophenone-3,
Benzophenone-4,
Benzophenone-5,
n-Hexyl 2-(4-diethylamino-2-hydroxybenzoyl) benzoate,
4-Methylbenzylidenecamphor,
Terephthalylidenedicamphorsulfonic acid,
Disodium phenyldibenzimidazoletetrasulfonate,
Anisotriazine,
Ethylhexyltriazone,
Diethylhexylbutamidotriazone,
Methylenebis (benzotriazolyl) tetramethylbutyiphenol,
Drometrizole trisiloxane,
Polysilicone-15,
1,1-Dicarboxy (2-2'-dimethylpropyl)-4,4-diphenyl-butadiene,
2,4-Bis [5-1 (dimethylpropyl)benzoxazol-2-yl(4-phenyl) imino]-6-(2-ethylhexyl)imino-1,3,5-triazine and mixtures thereof.

41. The solid UV-photoprotective composition as defined by claim 7, comprising one continuous fatty phase.

42. The solid UV-photoprotective composition as defined by claim 7, the same being anhydrous.

43. The solid UV-photoprotective composition as defined by claim 7, comprising up to 10% by weight of a hydrophilic phase, said hydrophilic phase optionally further comprising at least one water-soluble UV-screening agent.

44. The solid UV-photoprotective composition as defined by claim 43, said at least one water-soluble UV-screening agent comprising terephthalylidenedicamphorsulfonic acid.

45. The solid UV-photoprotective composition as defined by claim 7, said at least one oil being selected from the group consisting of volatile or non-volatile, polar or apolar hydrocarbon-based oils and/or silicone oils and/or fluoro oils, of animal, plant, mineral or synthetic origin and said at least one wax being selected from the group consisting of waxes of natural origin, waxes of mineral origin and waxes of synthetic origin, and mixtures thereof.

46. The solid UV-photoprotective composition as defined by claim 45, said at least one oil comprising from 20% to 80% by weight thereof and said at least one wax comprising from 5% to 40% by weight thereof.

47. The solid UV-photoprotective composition as defined by claim 7, said at least one fatty phase also comprising at least one fatty substance of pasty consistency of butter type.

48. The solid UV-photoprotective composition as defined by claim 7, further comprising at least one dyestuff or particles selected from the group consisting of pigments, nacres and fillers, and mixtures thereof.

49. The solid UV-photoprotective composition as defined by claim 7, shaped as a stick, a dish or a cast product.

50. A regime or regimen for the makeup of the lips and/or the face, comprising topically applying thereon a thus effective amount of the solid UV-photoprotecting composition as defined by claim 7.

51. A regime or regimen for the UV-photoprotection of the lips and/or the face, comprising topically applying thereon a thus effective amount of a solid UV-photoprotecting composition of claim 7.

52. A method for increasing the sun protection factor of a solid UV-photoprotecting composition comprising a) at least one fatty phase containing at least one oil and at least one wax, a UV-photoprotecting amount of b) at least one organic UV-screening agent and c) a fraction of metal oxide mineral nanopigments, said metal oxide nanopigments comprising octyltrimethoxysilane-coated titanium oxide nanopigments wherein said metal oxide nanopigments consist of particles with a mean elementary size of less than 100 nm, which comprises formulating therewith a thus effective amount of d) at least one octenylsuccinic anhydride-esterified starch salt, said composition being a solid having a shear force ranging from 100 to 300 g.

53. The solid UV-photoprotective composition as defined by claim 16, said titanium oxide mineral nanopigments having a mean elementary size ranging from 5 nm to 100 nm, said nanopigments comprising coated or uncoated titanium oxide in amorphous form or in rutile and/or anatase crystalline form.

54. The solid UV-photoprotective composition as defined by claim 16, said titanium oxide nanopigments having a hydrophobic coating.

55. The solid UV-photoprotective composition as defined by claim 54, said titanium oxide nanopigments having a hydrophobic coating having been treated with one or more compounds selected from the group consisting of alumina, silica, aluminum compounds, silicon compounds, sodium compounds, iron oxides, iron esters, fatty acids, fatty alcohols and derivatives thereof, lecithin, waxes, (meth)acrylic polymers and fluoro compounds, and mixtures thereof.

56. The solid UV-photoprotective composition as defined by claim 16, said titanium oxide nanopigments comprising from 0.01% to 20% by weight thereof, said at least one octenylsuccinic anhydride-esterified starch salt comprising from 0.1% to 10% by weight thereof, said at least one organic UV-screening agent comprising from 0.01% to 20% by weight thereof.

57. The solid UV-photoprotective composition as defined by claim 56, said at least one esterified starch salt being selected from the group consisting of:
aluminum starch octenylsuccinate,
sodium starch octenylsuccinate, and
calcium starch octenylsuccinate.

58. The solid UV-photoprotective composition as defined by claim 16, said UV-photoprotecting amount of butylmethoxydibenzoylmethane and octocrylene comprising from 0.01% to 20% by weight thereof.

59. The solid UV-photoprotective composition as defined by claim 16, comprising one continuous fatty phase.

60. The solid UV-photoprotective composition as defined by claim 16, the same being anhydrous.

61. The solid UV-photoprotective composition as defined by claim 16, comprising up to 10% by weight of a hydrophilic phase, said hydrophilic phase optionally further comprising at least one water-soluble UV-screening agent.

62. The solid UV-photoprotective composition as defined by claim 61, said at least one water-soluble UV-screening agent comprising terephthalylidenedicamphorsulfonic acid.

63. The solid UV-photoprotective composition as defined by claim 16, said at least one oil being selected from the group consisting of volatile or non-volatile, polar or apolar hydrocarbon-based oils and/or silicone oils and/or fluoro oils, of animal, plant, mineral or synthetic origin and said at least one wax being selected from the group consisting of waxes of natural origin, waxes of mineral origin and waxes of synthetic origin, and mixtures thereof.

64. The solid UV-photoprotective composition as defined by claim 63, said at least one oil comprising from 20% to 80% by weight thereof and said least one wax comprising from 5% to 40% by weight thereof.

65. The solid UV-photoprotective composition as defined by claim 16, said at least one fatty phase also comprising at least one fatty substance of pasty consistency of butter type.

66. The solid UV-photoprotective composition as defined by claim 16, further comprising at least one dyestuff or particles selected from the group consisting of pigments, nacres and fillers, and mixtures thereof.

67. The solid UV-photoprotective composition as defined by claim 16, shaped as a stick, a dish or a cast product.

68. A regime or regimen for the makeup and/or care of the lips and/or the face, comprising topically applying thereon a thus effective amount of the solid UV-photoprotecting composition as defined by claim 16.

69. A regime or regimen for the UV-photoprotection of the lips and/or the face, comprising topically applying thereon a thus effective amount of a solid UV-photoprotecting composition of claim 16.

70. A method for increasing the sun protection factor of a solid UV-photoprotecting composition comprising a) at least one fatty phase containing at least one oil and at least one wax, a UV-photoprotecting amount of b) butylmethoxydibenzoylmethane and octocrylene and c) a fraction of titanium oxide mineral nanopigments consisting of particles with a mean elementary size of less than 100 nm, which comprises formulating therewith a thus effective amount of d) at least one octenylsuccinic anhydride-esterified starch salt, said composition being a solid having a shear force ranging from 100 to 300 g.

71. The solid UV-photoprotective composition as defined by claim 17, said titanium oxide mineral nanopigments having a mean elementary size ranging from 5 nm to 100 nm, said nanopigments comprising coated or uncoated titanium oxide in amorphous form or in rutile and/or anatase crystalline form.

72. The solid UV-photoprotective composition as defined by claim 17, said titanium oxide nanopigments having a hydrophobic coating.

73. The solid UV-photoprotective composition as defined by claim 72, said titanium oxide nanopigments having a hydrophobic coating having been treated with one or more compounds selected from the group consisting of alumina, silica, aluminum compounds, silicon compounds, sodium compounds, iron oxides, iron esters, fatty acids, fatty alcohols and derivatives thereof, lecithin, waxes, (meth)acrylic polymers and fluoro compounds, and mixtures thereof.

74. The solid UV-photoprotective composition as defined by claim 17, said titanium oxide nanopigments comprising from 0.01% to 20% by weight thereof, said at least one octenylsuccinic anhydride-esterified starch salt comprising from 0.1% to 10% by weight thereof, and said UV-photoprotecting amount of butylmethoxydibenzoylmethane, octocrylene and drometrizole trisiloxane comprising from 0.01% to 20% by weight thereof.

75. The solid UV-photoprotective composition as defined by claim 17, said at least one esterified starch salt being selected from the group consisting of:
  aluminum starch octenylsuccinate,
  sodium starch octenylsuccinate, and
  calcium starch octenylsuccinate.

76. The solid UV-photoprotective composition as defined by claim 75, said at least one esterified starch salt comprising aluminum starch octenylsuccinate.

77. The solid UV-photoprotective composition as defined by claim 17, said UV-photoprotecting amount of butylmethoxydibenzoylmethane, octocrylene and drometrizole trisiloxane comprising from 0.01% to 20% by weight thereof.

78. The solid UV-photoprotective composition as defined by claim 17, comprising one continuous fatty phase.

79. The solid UV-photoprotective composition as defined by claim 17, the same being anhydrous.

80. The solid UV-photoprotective composition as defined by claim 17, comprising up to 10% by weight of a hydrophilic phase, said hydrophilic phase optionally further comprising at least one water-soluble UV-screening agent.

81. The solid UV-photoprotective composition as defined by claim 80, said at least one water-soluble UV-screening agent comprising terephthalylidenedicamphorsulfonic acid.

82. The solid UV-photoprotective composition as defined by claim 17, said at least one oil being selected from the group consisting of volatile or non-volatile, polar or apolar hydrocarbon-based oils and/or silicone oils and/or fluoro oils, of animal, plant, mineral or synthetic origin and said at least one wax being selected from the group consisting of waxes of natural origin, waxes of mineral origin and waxes of synthetic origin, and mixtures thereo.

83. The solid UV-photoprotective composition as defined by claim 82, said at least one oil comprising from 20% to 80% by weight thereof and said at least one wax comprising from 5% to 40% by weight thereof.

84. The solid UV-photoprotective composition as defined by claim 17, said at least one fatty phase also comprising at least one fatty substance of pasty consistency of butter type.

85. The solid UV-photoprotective composition as defined by claim 17, further comprising at least one dyestuff or particles selected from the group consisting of pigments, nacres and fillers, and mixtures thereof.

86. The solid UV-photoprotective composition as defined by claim 17, shaped as a stick, a dish or a cast product.

87. A regime or regimen for the makeup and/or care of the lips and/or the face, comprising topically applying thereon a thus effective amount of the solid UV-photoprotecting composition as defined by claim 17.

88. A regime or regimen for the UV-photoprotection of the lips and/or the face, comprising topically applying thereon a thus effective amount of a solid UV-photoprotecting composition of claim 17.

89. A method for increasing the sun protection factor of a solid UV-photoprotecting composition comprising a) at least one fatty phase containing at least one oil and at least one wax, a UV-photoprotecting amount of b) butylmethoxydibenzoylmethane, octocrylene and drometrizole trisiloxane and c) a fraction of titanium oxide mineral nanopigments consisting of particles with a mean elementary size of less than 100 nm, which comprises formulating therewith a thus effective amount of d) at least one octenylsuccinic anhydride-esterified starch salt, said composition being a solid having a shear force ranging from 100 to 300 g.

* * * * *